United States Patent
Giles et al.

(10) Patent No.: US 12,280,131 B2
(45) Date of Patent: Apr. 22, 2025

(54) DEPOSITION SYSTEM FOR HAIR

(71) Applicant: Conopco, Inc., Englewood Cliffs, NJ (US)

(72) Inventors: Colin Christopher David Giles, Wirral (GB); Rongrong Zhou, Wirral (GB)

(73) Assignee: Conopco, Inc., Englewood Cliffs, NY (US)

( * ) Notice: Subject to any disclaimer, the term of this patent is extended or adjusted under 35 U.S.C. 154(b) by 834 days.

(21) Appl. No.: 17/413,361

(22) PCT Filed: Dec. 5, 2019

(86) PCT No.: PCT/EP2019/083916
§ 371 (c)(1),
(2) Date: Jun. 11, 2021

(87) PCT Pub. No.: WO2020/126532
PCT Pub. Date: Jun. 25, 2020

(65) Prior Publication Data
US 2022/0287933 A1 Sep. 15, 2022

(30) Foreign Application Priority Data
Dec. 19, 2018 (EP) .................................... 18213907

(51) Int. Cl.
*A61K 8/34* (2006.01)
*A61K 8/27* (2006.01)
*A61K 8/41* (2006.01)
*A61K 8/49* (2006.01)
*A61Q 5/00* (2006.01)
*A61Q 5/12* (2006.01)

(52) U.S. Cl.
CPC ................ *A61K 8/342* (2013.01); *A61K 8/27* (2013.01); *A61K 8/416* (2013.01); *A61K 8/4933* (2013.01); *A61Q 5/006* (2013.01); *A61Q 5/12* (2013.01); *A61K 2800/596* (2013.01)

(58) Field of Classification Search
CPC .......... A61K 8/342; A61K 8/27; A61K 8/416; A61K 8/4933; A61K 2800/596; A61Q 5/006; A61Q 5/12
See application file for complete search history.

(56) References Cited

U.S. PATENT DOCUMENTS

| | | | | |
|---|---|---|---|---|
| 2014/0120048 A1* | 5/2014 | Krueger | ................... | A61P 31/10 424/70.11 |
| 2015/0150774 A1* | 6/2015 | Kruger | ..................... | A61K 8/42 424/94.1 |
| 2015/0272865 A1* | 10/2015 | Mette | ........................ | A61K 8/64 424/94.1 |
| 2015/0297485 A1* | 10/2015 | Kleinen | ............... | A61K 8/4973 514/786 |
| 2016/0081907 A1 | 3/2016 | Schwab et al. | | |
| 2016/0083333 A1 | 3/2016 | Schwab et al. | | |

FOREIGN PATENT DOCUMENTS

| | | | | |
|---|---|---|---|---|
| DE | 102015223028 | 6/2016 | | |
| EP | 0530974 | 3/1993 | | |
| EP | 2216010 A1 * | 8/2010 | ............... | A61K 8/02 |
| EP | 2457556 | 5/2012 | | |
| EP | 2457556 A2 * | 5/2012 | ............. | A61K 8/442 |
| WO | WO9631188 | 10/1996 | | |
| WO | WO2004093834 | 11/2004 | | |
| WO | WO2009138194 | 11/2009 | | |
| WO | WO2014056962 | 4/2014 | | |
| WO | WO2017066500 | 4/2017 | | |

OTHER PUBLICATIONS

Machine translation for EP-2457556-A2 (Year: 2012).*
Cetearyl alcohol; https://pubchem.ncbi.nlm.nih.gov/compound/62238; cetearyl alcohol mixture of C16 and C18 fatty alcohols; site accessed Jan. 2024 (Year: 2016).*
Cetrimonium Chloride; https://cosmetics.specialchem.com/inci-ingredients/cetrimonium-chloride; site accessed Feb. 2024 (Year: 2023).*
Dioleoylisopropyl Dimonium Methosulfate; https://drugs.ncats.io/substance/YOI7EU4P4G; site accessed Feb. 2024 (Year: 2024).*
Dioleoylisopropyl Dimonium Methosulfate benefits; https://cosmileeurope.eu/inci/detail/4778/dioleoylisopropyl-dimonium-methosulfate; site accessed Aug. 2024 (Year: 2024).*
Search Report and Written Opinion in EP18213907; Feb. 26, 2019.
Search Report and Written Opinion in PCTEP2019083916; Feb. 17, 2020.
IPRP2 in PCTEP2019083916; Dec. 22, 2020.

* cited by examiner

*Primary Examiner* — Robert A Wax
*Assistant Examiner* — John W Lippert, III
(74) *Attorney, Agent, or Firm* — Byrne Poh LLP; Nina R. Horan

(57) ABSTRACT

A hair treatment composition comprising: a) a conditioning base comprising: i) a cationic conditioning surfactant having from 16 to 32 carbon atoms; ii) a fatty alcohol having from 8 to 22 carbon atoms; and b) from 0.1 to 10 wt % of metal pyrithiones and mixtures thereof; wherein the composition further comprises: (c) from 0.1 to 5 wt % of a diesterquat; and wherein the ratio of b) to c) is from 1:1 to 1:0.1, provides improved deposition of metal pyrithione on hair surfaces.

20 Claims, No Drawings

DEPOSITION SYSTEM FOR HAIR

CROSS-REFERENCE TO RELATED APPLICATIONS

This application is a U.S. 371 National Stage Application of PCT International Application No. PCT/EP2019/083916, with international filing date of Dec. 5, 2019, which claims the benefit of and priority to European patent application No. 18213907.1 filed Dec. 19, 2018, the contents of which are incorporated herein by reference in their entireties.

FIELD OF THE INVENTION

The present invention relates to hair treatment compositions containing a diester quat and the use of these compositions to deposit antidandruff actives on hair and scalp surfaces.

BACKGROUND AND PRIOR ART

US2016081907 (Evonik) discloses hair formulations containing liquid ester quats and/or imidazolinium salts that are made stable for over a long term by the addition of carbomers or other polymers. US2016083333 discloses cosmetic formulations containing mixed ester quats for cosmetically treating keratin fibres.

DE102015223028 (Henkel) discloses a cosmetic composition for treating keratin fibers, containing in a cosmetic carrier, a) at least one specified esterquat in an amount of 0.01 to 20.0 weight %, based on the weight of the total composition, and b) at least a further different from a) cationic and/or cationizable compound in an amount of 0.01 to 20.0 weight %.

It has now been found that a combination of particular esterquats with a hair treatment composition that comprises zinc pyrithione provides improved deposition of the zinc pyrithione to hair.

DEFINITION OF THE INVENTION

In a first aspect, the present invention provides a hair treatment composition comprising:
a) a conditioning base comprising:
  i) a cationic conditioning surfactant having from 16 to 32 carbon atoms;
  ii) a fatty alcohol having from 8 to 22 carbon atoms; and
b) from 0.05 to 10 wt % of an antidandruff active selected from metal pyrithiones and mixtures thereof;
wherein the composition further comprises:
(c) from 0.1 to 5 wt % of a diesterquat.

In a second aspect the invention provides a method of treating hair comprising the step of applying the hair a composition of the first aspect of the invention.

In a third aspect the invention provides a use of a diesterquat to deposit an antidandruff active selected from metal pyrithiones and mixtures thereof on hair.

GENERAL DESCRIPTION OF THE INVENTION

The Cationic Conditioning Surfactant

Conditioner compositions will comprise a cationic conditioning surfactant, which is cosmetically acceptable and suitable for topical application to the hair.

Preferably, the cationic conditioning surfactants have the formula $N^+(R^1)(R^2)(R^3)(R^4)$, wherein $R^1$, $R^2$, $R^3$ and $R^4$ are independently ($C_1$ to $C_{30}$) alkyl or benzyl.

Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl.

More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic conditioning-surfactants for use in conditioner compositions according to the invention include cetyltrimethylammonium chloride (CTAC), behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (e.g., Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Preferably, the cationic surfactant is selected from cetyltrimethylammonium chloride and behenyltrimethylammonium chloride, most preferably behenyltrimethylammonium chloride.

Another example of a class of suitable cationic surfactants for use in the invention, either alone or together with one or more other cationic surfactants, is a combination of (i) and (ii) below:
  (i) an amidoamine corresponding to the general formula (II):

$$R1CONH(CH2)mN(R2)R3 \qquad (II)$$

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and
  (ii) an acid.

As used herein, the term hydrocarbyl chain means an alkyl or alkenyl chain.

Preferred amidoamine compounds are those corresponding to formula (I) in which
  $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethyl-amine, behenamidopropyldiethylmine, behenamidoethyldiethylamine, behenamidoethyldimethylamine, arachidamidopropyl-dimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pennsylvania, USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton New Jersey, USA).

Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

In conditioners for use in the invention, the level of cationic conditioning surfactant will generally range from 0.01 to 10%, more preferably 0.05 to 7.5%, most preferably 0.1 to 5% by total weight of cationic conditioning surfactant based on the total weight of the composition.

The Fatty Alcohol

The compositions of the invention comprise a fatty alcohol having a carbon-carbon chain length of from $C_8$ to $C_{22}$.

The combined use of fatty alcohols and cationic surfactants in conditioning compositions is preferred because this leads to the formation of a lamellar phase, in which the cationic surfactant is dispersed.

The fatty alcohol comprises from 8 to 22 carbon atoms, preferably 16 to 22, most preferably C16 to C18. Fatty alcohols are typically compounds containing straight chain alkyl groups. Preferably, the alkyl groups are saturated. Examples of preferred fatty alcohols include cetyl alcohol, stearyl alcohol and mixtures thereof. The use of these materials is also advantageous in that they contribute to the overall conditioning properties of compositions for use in the invention.

The level of fatty alcohol in conditioners for use in the invention will generally range from 0.01 to 10%, preferably from 0.1 to 8%, more preferably from 0.2 to 7%, most preferably from 0.3 to 6% by weight of the composition.

The weight ratio of cationic-surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

The Antidandruff Agent

The composition of the invention comprises (suspended particles of metal pyrithiones) an antidandruff agent.

Antidandruff agents are compounds that are active against dandruff and are typically antimicrobial agents, preferably antifungal agents. Antidandruff agents typically display a minimum inhibitory concentration of about 50 mg/ml or less against *Malassezia*.

The total amount of anti-dandruff agent is preferably present at levels of from 0.05% to 10%, preferably 0.1% to 5% and most preferably 0.2% to 4% by weight of the total composition.

However, where the anti-dandruff agent is zinc pyrithione, preferred levels in compositions of the invention are from 0.1 to 3%, more preferably from 0.2 to 2%, most preferably from 0.5 to 1.5%, by weight based on the total weight of the composition.

The antidandruff agent is selected such that it is insoluble in the composition of the invention and, therefore, capable of forming suspended particles. The solubility of the antidandruff agent will vary according to the presence and level of the other ingredients.

The antidandruff agent is selected from metal pyrithiones. Suitable metal pyrithiones include zinc pyrithione, copper pyrithione, silver pyrithione, zirconium pyrithione, and mixtures thereof. The most preferred metal pyrithione is zinc pyrithione.

The particles of the zinc pyrithione may be amorphous, or may take various regular or irregular crystalline forms such as rods, needles, blocks, platelets and mixtures thereof. The average particle diameter of the zinc pyrithione particles (maximum dimension) is typically from about 0.1 to about 50 μm, preferably from about 0.1 μm to about 10 μm, more preferably from about 0.1 μm to about 5 μm as determined, for example, using a Horiba LA-910 Laser scattering particle size distribution analyzer.

Additional Optional Anti-Dandruff Agents

The compositions of the invention may include an additional optional anti-dandruff agent that is soluble within the cleansing compositions of the present invention. These are preferably selected from azoles (preferably selected from ketoconazole and climbazole), octopirox (piroctone olamine), selenium sulfide, salicylic acid and combinations thereof.

Optional Zinc Salts

The compositions of the invention advantageously include a zinc salt.

The additional zinc salt may suitably be selected from zinc salts of organic acids, zinc salts of inorganic acids, zinc oxides, zinc hydroxides and mixtures thereof.

Examples of additional zinc salts for use in the invention include zinc oxide, zinc pyrrolidone carboxylic acid, zinc citrate, zinc carbonate, zinc chloride, zinc sulphate, zinc glycinate, zinc acetate, zinc lactate, and mixtures thereof.

Additional zinc salts for use in the formulated products of the invention preferably have a zinc mass % of at least 25%, more preferably at least 30% (based on total mass of the zinc salt).

Additional zinc salts for use in the invention preferably have a solubility in water of 20 g/l or less, more preferably 0.1 g/l or less at 25° C.

Examples of preferred additional zinc salts for use in the invention include zinc oxide, zinc pyrrolidone carboxylic acid, zinc citrate, zinc carbonate and mixtures thereof.

The level of additional zinc salt(s) in compositions of the invention generally ranges from 0.1 to 5%, and preferably ranges from 0.2 to 3%, more preferably from 0.25 to 2.5%, by weight based on the total weight of the composition.

In a particularly preferred composition according to the invention the additional zinc salt is selected from zinc oxide, zinc pyrrolidone carboxylic acid, zinc citrate, zinc carbonate and mixtures thereof; at a level ranging from about 0.25 to about 2.5% by weight based on the total weight of the composition.

The Diester Quat

As ingredient iv), the inventive compositions comprise at least one ester quat, preferably of the structure shown below (I):

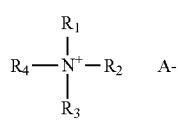
(I)

R3 and R4 are —X—O—CO—R5

Wherein, the radicals R1, R2 each independently of each other can be identical or different.

The radicals R1, R2 represent:
a branched or unbranched alkyl radical having 1 to 4 carbon atoms, preferably selected from the group selected from methyl, ethyl, propyl, iso-propyl, butyl, tert-butyl or iso-butyl, more preferably methyl, ethyl, propyl, and isopropyl and most preferably methyl.

R3 and R4 are represented by —X—O—CO—R5, wherein:
X is a branched or unbranched alkyl group having 1 to 4 carbon atoms, preferably selected from methyl, ethyl, propyl, iso-propyl, butyl, tert-butyl or iso-butyl, more preferably ethyl, propyl or isopropyl and most preferably selected from ethyl and isopropyl.

R5 is selected from a saturated branched or unbranched, an unsaturated branched or unbranched, or a cyclic saturated or unsaturated alkyl radical, each having 6 to 30, preferably 12 to 24, more preferably 14 to 20 carbon atoms and which may contain a hydroxyl group. R5 is preferably selected from a saturated or unsaturated branched alkyl radical, more preferably a saturated branched alkyl radical.

A is a physiologically compatible organic or inorganic anion. A is selected from the halide ions, fluoride, chloride, bromide, iodide, sulfates of the general formula $RSO_3^-$, wherein R is a saturated or unsaturated alkyl radical having 1 to 4 carbon atoms, with anionic radicals of organic acids such as maleate, fumarate, oxalate, tartrate, citrate, lactate or acetate. A preferred sulphates are methosulphate and ethanesulphate. Most preferably, $A^-$ is selected from chloride, ethanesulphate or methosulphate.

In a preferred embodiment, R3 and R4 have —X— that is selected from ethyl and isopropyl, R5 has chains selected from i) branched, saturated chains with a chain length of C18 or C16 and ii) unbranched, unsaturated or saturated chains, with a chain length of C18 or C16.

Examples of such compounds are preferably Dioleoylisopropyl Dimonium methosulfate, Dioleoylisopropyl Dimonium Chloride, Dipalmoylisopropyl Dimonium methosulfate, Dipalmoylisopropyl Dimonium Chloride, bis (Isostearoyl/oleoyl isopropyl) Dimonium methosulfate, bis (Isostearoyl/oleoyl isopropyl) Dimonium chlorides.

A highly preferred compound carries the name bis (Isostearoyl/oleoyl isopropyl) Dimonium methosulfate and is designated by the INCI nomenclature as Quaternium-98 and is commercially available under the name Varisoft® EQ 100 from Evonik. A further preferred compound is available under the name Varisoft® EQ 65 also from Evonik.

The esterquats corresponding to formula (I) are present in the inventive compositions in amounts of from 0.1 to 5 wt %, preferably 0.1 to 2, more preferably 0.5 to 1.5, even more preferably 0.5 to 1.2, most preferably 0.6 to 1 wt % based on the total weight of the composition.

The ratio of silicone (b) to diesterquat (c) is from 1:1 to 1:0.1, preferably 1:0.2 to 1:0.4, most preferably from 1:0.25 to 1:0.4.

Further Ingredients

The Silicone

The compositions of the invention preferably contain, emulsified droplets of a silicone conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. Preferably, the silicone is selected from the group consisting of dimethicone, dimethiconol, amodimethicone and mixtures thereof. Also preferred are blends of amino-functionalised silicones with dimethicones.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in shampoos and conditioners of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone". A preferred amodimethicone is commercially available from Dow Corning as DC 7134.

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.1 wt % to 10% wt of the total composition more preferably from 0.1 wt % to 5 wt %, most preferably 0.5 wt % to 3 wt % is a suitable level.

The composition according to the invention may comprise any of a number of ingredients which are common to conditioning compositions Other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

In a second aspect there is provided a method for the manufacture of a conditioning composition according to the first aspect. The method comprising forming a conditioning gel phase which comprises a cationic surfactant and a fatty material and, separately forming a solution of the hydrophobically modified polymer, optionally with a cationic surfactant, which, if present, is added to the water first.

The two mixtures are then added to one another before the remaining ingredients are added to form the conditioning composition.

Preferably, the extra ingredients include perfumes, thickeners and preservatives.

The invention will now be illustrated by the following non-limiting Examples:

EXAMPLES

The invention will now be illustrated by the following non-limiting Examples:

Example 1: Compositions for Treatment of Hair Prior to Anitdandruff Deposition Analysis Four hair conditioner formulations (designated A, B, 1 and 2) were used to treat hair prior to antidandruff active deposition analysis. The antidandruff active was zinc pyritione. Compositions 1 and 2 were in accordance with the invention; A and B were comparative compositions. The compositions are given in Table 1.

TABLE 1

| Compositions of Conditioners A, B, C and D | | | | | |
|---|---|---|---|---|---|
| INCI | Active Level | A | B | 1 | 2 |
| Bis(Isotearoyl/ Oleoyllsoproypl) Dimonium Methosulfate (Varisoft EQ100) | 100 | 0 | 0 | 0.8 | 0.8 |
| Behentrimonium Chloride | 70 | 2.29 | 2.29 | 1.14 | 1.14 |
| Cetearyl Alcohol | 100 | 3.2 | 3.2 | 3.2 | 3.2 |
| Dimethicone 600K and Amodimethicone 2000 nm | 70 | 3.57 | 3.57 | 3.57 | 3.57 |
| Zinc Pyrithione | 50 | 0.5 | 1 | 0.5 | 1 |
| Perfume | 100 | 0.6 | 0.6 | 0.6 | 0.6 |
| Preservatives | 100 | 0.5 | 0.5 | 0.5 | 0.5 |
| Water | 100 | To 100 | To 100 | To 100 | To 100 |

Formulations were made by adding the cationic surfactants to the fatty alcohol and stirring at 85° C. Gradually this mixture was added to water, typically at 55° C., such that the mixture temperature was 60° C. This temperature was maintained for 30 minutes with stirring. The mixture was then cooled towards ambient by adding more water, and other ambient temperature ingredients, and using external cooling if required, and stirred.

Example 2: Treatment of Hair with Compositions A, B, 1 and 2 for Zinc Pyrithione Deposition Measurements in Accordance with the Invention The hair used was Chinese virgin hair, in switches of 5 g weight and 6 inch length.

The hair was treated with Compositions A, B, 1 and 2 as follows:—

Hair was first treated with a cleansing shampoo using the following method:—

The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 30 seconds.

The wet hair was then treated with Conditioner A or B or 1 or 2 using the following method:—

Conditioner was applied to the wet hair at a dose of 0.2 g of conditioner per 1 g of hair and massaged into the hair for 1 minute. The hair was rinsed under running water for 1 minute and excess water removed. Hair was dried overnight at room temperature.

5 replicates hair switches were prepared for each conditioner. The hair was then cut and mounted to the 40 mm plastic rings, zinc pyrithione deposition on hair was measured by Intertec Manchester using X-Ray Fluorescence Spectrometer (XRF) and calibrated with appropriate standards.

Zinc pyrithione deposition measured on hair switches treated with Conditioners A, B, 1 and 2 are given in the Table 2, and shown graphically in FIG. 1.

TABLE 2

Zinc deposition data for hair treated with Conditioners A, B, 1 and 2.

| Conditioner | Average Zinc deposition (ppm) | Stdev |
|---|---|---|
| A | 273.48 | 46.48 |
| B | 350.51 | 89.49 |
| 1 | 410.49 | 38.65 |
| 2 | 498.19 | 91.53 |

It will be seen that the zinc pyrithione deposition for hair treated with Conditioners 1 and 2 has higher deposition of zinc pyrithione. Conditioner A and 1 have same amount of 0.25% ZnPTO. Compare with Conditioner A, Conditioner 1 has higher Zinc deposition which is linked to the diesterquat (Varisoft EQ100) inside the formulation. Conditioner B and 2 have 0.5% ZnPTO, and conditioner 2 with the diesterquat (Varisoft EQ100) has higher Zinc deposition.

The invention claimed is:

1. A hair treatment composition consisting of:
   a) a conditioning base consisting of:
      i) from 0.01 to 10 wt % of a cationic conditioning surfactant or mixtures thereof, the cationic conditioning surfactant having from 16 to 32 carbon atoms;
      ii) from 0.01 to 10 wt % of a fatty alcohol or mixtures thereof, the fatty alcohol having from 8 to 22 carbon atoms;
   b) from 0.05 to 10 wt % of zinc pyrithione;
   c) from 0.1 to 5 wt % of a diesterquat, selected from bis (isostearoyl/oleoyl isopropyl) dimonium methosulfate or dioleoylisopropyl dimonium methosulfate;
   d) optionally from 0.01 to 10 wt % of a silicone selected from the group consisting of dimethicone, dimethiconol, amodimethicone and mixtures thereof;
   e) optionally an ingredient selected from the group consisting of perfumes, thickeners, and preservatives; and
   f) water.

2. The composition of claim 1, wherein the diesterquat is present in an amount of from 0.5 to 1.2 wt % based on the total weight of the composition.

3. The composition claim 1, wherein the zinc pyrithione is present in an amount of from 0.1 to 3%, by weight based on the total weight of the composition.

4. A method of treating hair comprising applying to the hair a composition of claim 1.

5. The composition of claim 3, wherein the zinc pyrithione is present in an amount of from 0.2 to 2%, by weight based on the total weight of the composition.

6. The composition of claim 3, wherein the zinc pyrithione is present in an amount of from 0.5 to 1.5%, by weight based on the total weight of the composition.

7. The composition of claim 1, wherein the diesterquat is bis(isostearoyl/oleoyl isopropyl) dimonium methosulfate.

8. The composition of claim 1, wherein the diesterquat is dioleoylisopropyl dimonium methosulfate.

9. The composition of claim 1, wherein the cationic conditioning surfactant is present in an amount from 0.05 to 7.5%, by weight based on the total weight of the composition.

10. The composition of claim 1, wherein the cationic conditioning surfactant is present in an amount from 0.1 to 5%, by weight based on the total weight of the composition.

11. The composition of claim 1, wherein the fatty alcohol is present in an amount from 0.1 to 8%, by weight based on the total weight of the composition.

12. The composition of claim 1, wherein the fatty alcohol is present in an amount from 0.2 to 7%, by weight based on the total weight of the composition.

13. The composition of claim 1, wherein the fatty alcohol is present in an amount from 0.3 to 6%, by weight based on the total weight of the composition.

14. The composition of claim 1, wherein the diesterquat is present in an amount of from 0.1 to 2 wt % based on the total weight of the composition.

15. The composition of claim 1, wherein the diesterquat is present in an amount of from 0.5 to 1.5 wt % based on the total weight of the composition.

16. The composition of claim 1, wherein the diesterquat is present in an amount of from 0.6 to 1 wt % based on the total weight of the composition.

17. The composition of claim 1, wherein the cationic conditioning surfactant is selected from cetyltrimethylammonium chloride (CTAC), behenyltrimethylammonium chloride (BTAC), behentrimonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride, cocotrimethylammonium chloride, PEG-2-oleammonium chloride, the corresponding hydroxides thereof, and mixtures thereof.

18. The composition of claim 1, wherein the fatty alcohol comprises from 16 to 22 carbon atoms.

19. The composition of claim 1, wherein the fatty alcohol is selected from cetyl alcohol, stearyl alcohol, and mixtures thereof.

20. The composition of claim 1, wherein the silicone selected from dimethicone, amodimethicone, and mixtures thereof.

* * * * *